United States Patent [19]

Hentsche et al.

[11] 4,271,297

[45] Jun. 2, 1981

[54] PROCESS FOR THE PRODUCTION OF SUSPENSION OR SOLUTIONS OF CYANURIC CHLORIDE IN ORGANIC SOLVENTS (I)

[75] Inventors: Klaus Hentschel, Kalmthout, Belgium; Friedrich Bittner, Bad Soden; Gerd Schreyer, Hanau, both of Fed. Rep. of Germany

[73] Assignee: Deutsche Gold-und Silber-Scheideanstalt vormals Roessler, Frankfurt, Fed. Rep. of Germany

[21] Appl. No.: 94,872

[22] Filed: Nov. 16, 1979

[30] Foreign Application Priority Data

Nov. 20, 1978 [DE] Fed. Rep. of Germany ....... 2850308

[51] Int. Cl.³ .......................................... C07D 251/28
[52] U.S. Cl. ..................................................... 544/190
[58] Field of Search ........................................... 544/190

[56] References Cited

U.S. PATENT DOCUMENTS

| | | | |
|---|---|---|---|
| 3,256,070 | 6/1966 | Trickey | 23/294 |
| 3,925,377 | 12/1975 | Geiger et al. | 260/248 |
| 4,017,413 | 4/1977 | Bittner et al. | 252/187 R |

FOREIGN PATENT DOCUMENTS

| | | |
|---|---|---|
| 1545840 | 10/1969 | Fed. Rep. of Germany . |
| 1964619 | 7/1970 | Fed. Rep. of Germany . |
| 1670731 | 12/1970 | Fed. Rep. of Germany . |
| 1695117 | 3/1972 | Fed. Rep. of Germany . |
| 2332636 | 1/1975 | Fed. Rep. of Germany . |
| 2454910 | 8/1976 | Fed. Rep. of Germany . |

OTHER PUBLICATIONS

Rys, *Helv. Chem. Acta*, vol. 54, pp. 163–176.
Ullmann, "Enzyklopädie der technishen Chemie", 3rd ed., (1954), vol. 1, pp. 743–744 and 769–770.
Ibid. vol. 5, pp. 624–625.

*Primary Examiner*—John M. Ford
*Attorney, Agent, or Firm*—Cushman, Darby & Cushman

[57] ABSTRACT

Suspension or solutions of cyanuric chloride in water containing organic solvents are prepared at high mixing velocities and low temperatures with resulting low degree of hydrolysis by introducing liquid cyanuric chloride through a nozzle in the upper portion of the mixing apparatus in countercurrent flow to upwardly flowing solvent introduced from at least one lower nozzle above a breast shaped constriction in the lower, open portion of the apparatus. In this way the chamber walls are always covered with an unbroken layer of liquid. The process can be carried out at normal, reduced or elevated pressure. At reduced pressure by evaporation of the solvent there is simultaneously a cooling of the system.

9 Claims, 3 Drawing Figures

PROCESS FOR THE PRODUCTION OF SUSPENSION OR SOLUTIONS OF CYANURIC CHLORIDE IN ORGANIC SOLVENTS (I)

BACKGROUND OF THE INVENTION

Cyanuric chloride which is produced by the trimerization of cyanogen chloride with the help of catalysts, above all activated carbon, as is known is a very interesting intermediate product in various industrial sectors such as the production of dyestuffs and products for the textile industry, as well as for pharmaceuticals, products for agriculture, as well as for the synthetic resin, rubber and explosive industries.

As is known after the trimerization cyanuric chloride is obtained in gaseous form, together with unreacted cyanogen chloride and chlorine, as well as byproducts.

For a long time it was customary to convert this gaseous reaction mixture directly into solid cyanuric chloride, e.g. by leading the gaseous mixture into a chamber cooled from outside (see Ullmann, Enzyklopadie der technischen Chemie, 3rd edition, 1954 Vol. 5, pages 624–625 and 4th edition, 1975 Vol. 9, pages 652), or by introducing it into a ball mill cooled with water according to the process of Trickey U.S. Pat. No. 3,256,070.

Solid cyanuric chloride generally is obtained in powder form and until now has been further processed predominantly in this form.

In order to increase its reaction velocity in the further processing it is desirable to have the cyanuric chloride present either in finely divided or dissolved form.

For this purpose there are known a series of processes in which cyanuric chloride in solid form is introduced into an organic solvent (Tandon, German AS No. 1965840) or into strongly cooled organic solvent-water systems (Grauer, German AS No. 1695177) whereupon the thus obtained cyanuric chloride solutions or suspensions are reacted as soon as possible after their production.

However, a problem in the production of these kinds of suspensions or solutions is the easy hydrolyzability of cyanuric chloride to cyanuric acid, which begins already in the presence of small amounts of water, as are present, e.g., in industrial solvents, and in a given case can progress up to explosions, entirely apart from the losses of cyanuric chloride, itself, see R. Rys, A. Schmitz and H. Zollinger, Helv. Chem. Acta, Vol. 54, 1, 14 (1971), pages 163–176.

Precisely industrial solvents, thus organic-aqueous systems, however, on account of their ready accessibility for the production of cyanuric chloride suspensions or solutions are of particular significance.

Of course, it is known that a neutral, aqueous suspension of cyanuric chloride is obtained if molten cyanuric chloride is allowed to run into water, see Wojahn, German Pat. No. 1670731.

However, the thus obtained suspension was of the pure aqueous type, i.e. free from organic solvent, which as is known increase the dissolving power for cyanuric chloride and therewith the danger of its hydrolysis to cyanuric acid in the presence of water.

This kind of hydrolysis can reach such speeds in aqueous organic solvents that explosions occur.

The process of Wojahn, German Pat. No. 1670731 does not permit the conversion to organic-aqueous systems since the residence times of cyanuric chloride suspensions in the indicated apparatus was too long, particularly if there is simultaneously considered the mixing temperatures of solvent and cyanuric chloride.

Thus, according to the data in the mentioned patent, at a mixing ratio of water to cyanuric chloride of 4:1 the mixing temperature of the aqueous suspension is almost 50° C., if water of 20° C. is added in order to produce a suspension from the cyanuric chloride melt. At lower mixing ratios the mixing temperature was even far higher.

Higher mixing ratios than 4:1 according to the data of the mentioned patent do not result in a considerable reduction of the mixing temperature since this approaches a limiting value which in using water at 20° C. lies at about 45° C.

Since the apparatus employed only can be operated at normal pressure, it was not possible to simultaneously lower the temperature by lowering the pressure and therewith set up lower mixing temperatures.

The object of the invention therefore is the production of cyanuric chloride suspensions or solutions in water containing organic solvents while avoiding or greatly reducing the hydrolysis of the cyanuric chloride.

SUMMARY OF THE INVENTION

Figure 1:
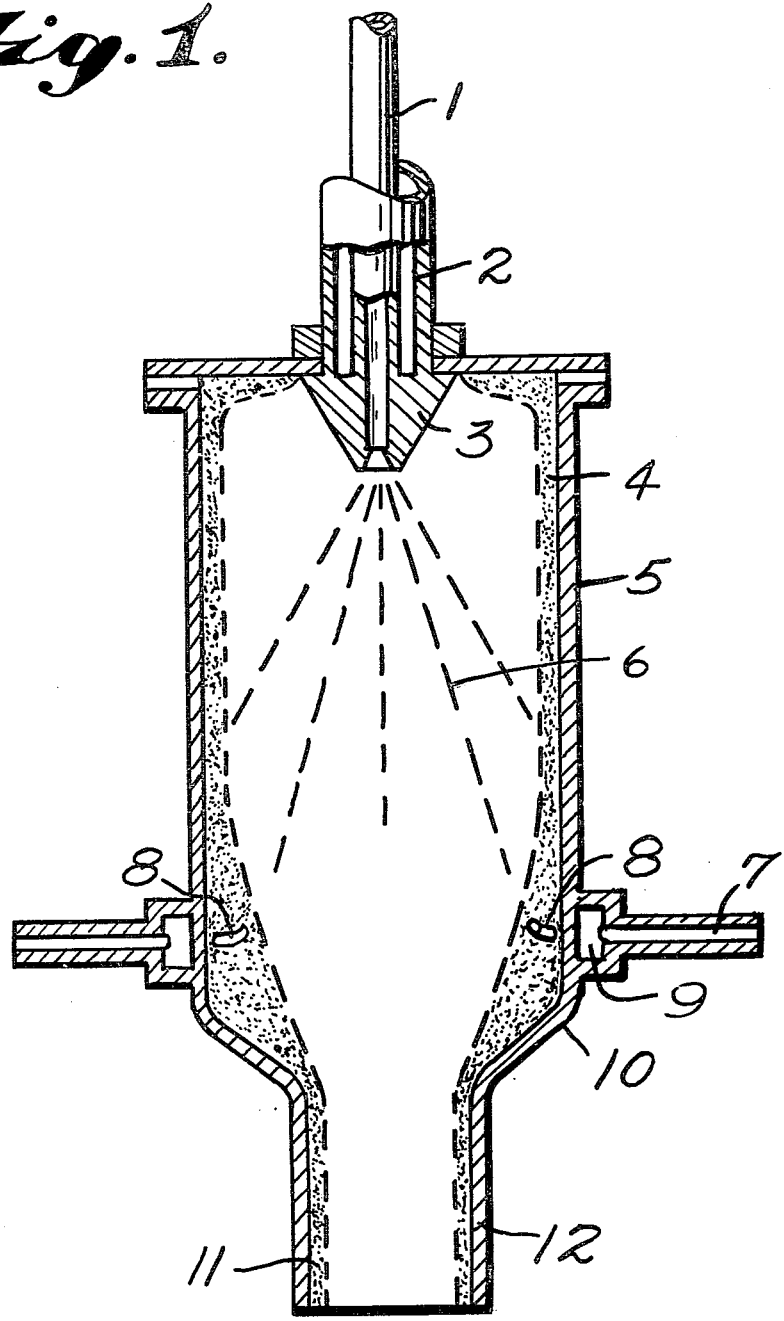
FIG. 1 is a vertical sectional elevation of one form of apparatus suitable for carrying out the process of the invention.

It has now been found that suspensions or solutions of cyanuric chloride can be produced while avoiding or very greatly reducing the hydrolysis of cyanuric chloride by bringing into contact liquid cyanuric chloride and aqueous organic solvent with the help of a nozzle if liquid cyanuric chloride which is preferably free from chlorine and cyanogen chloride is sprayed into a container at temperatures in its molten range, if necessary in the presence of an inert gas, through a nozzle, preferably a spray nozzle, which is located in the head of a tubular container, during which this tubular container is closed or closeable at the top and downward constricted breast shaped to a discharge opening and with which the water containing organic solvent discharges through one or preferably several nozzles, preferably polished steel nozzles, which are located above the constriction and consist of one or more tangential spray agencies arranged in one or more rows which are arranged slightly above in the direction of the upper closing device or are arranged in the direction of the nozzle located in the upper portion and form a liquid layer along the entire chamber walls up to the nozzle for the cyanuric chloride, whereby the thickness of this layer at the breast shaped restriction is greater than at the rest of the chamber walls, and in which the sprayed cyanuric chloride enters.

The liquid cyanuric chloride is preferably introduced into the nozzle through a heated conduit.

By using the described apparatus it is possible to so distribute the water containing organic solvent at the chamber walls that the liquid layer at the breast shaped constriction is thicker than at the remaining chamber walls.

By the expression used in the glass art: "breast shaped constriction" is meant a constriction which does not proceed steeply, but in a flat S curve going from the wall of the tubular container to the discharge opening. Corresponding constrictions are also present in red wine bottles at the transition from the true bottle to the neck.

The constriction in the tubular container can preferably always begin where about 50% of the sprayed particles meet the liquid layer built up on the wall. Preferably this is the case in the lower third of the tubular container.

The size of the diameter of the discharge opening of itself is not critical. Naturally it depends on the viscosity of the medium being discharged and must have at least such a size that air can enter.

The discharge opening is preferably converted into a discharge tube which has any desired diameter, preferably however, the same diameter or larger than the discharge opening.

The nozzle or nozzles for the water containing organic solvent to be sure can be arranged at any place in the tubular container above the constriction, but preferably are located in the region directly above the breast shaped constriction.

As the tangentially arranged spray agencies, there can be used small tubes or nozzles as well as openings in the chamber walls or, with the presence of a feed ring, in its chamber walls.

Preferably there are used small tubes.

The tubular container described has the great advantage that it can be operated not only at an atmospheric pressure but also at reduced pressure. Thus without doing anything further it permits the adjustment proceeding from atmospheric pressure to reduced pressure of 0.01 bar.

The discharging mixture which leaves the tubular container 5 through the discharge opening 12 goes to the container 14 which can be connected if desired detachably, either directly or indirectly via line 13 to the discharge opening 12 of the container 5.

Figure 3:
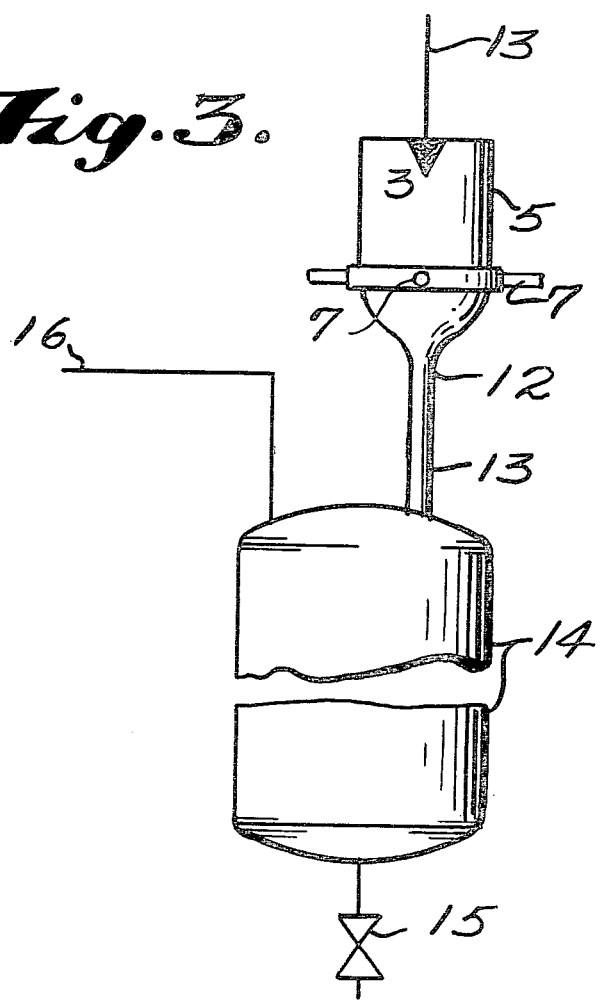
FIG. 3 is a schematic view of apparatus for carrying out the invention.

In this way it is possible to establish any desired pressure, i.e., any reduced or excess pressure, in the tubular container 5 and container 14 through known apparatus which is connected with the container 14 via line 16, see FIG. 3. (However, the known apparatuses for regulating the pressure are not shown in FIG. 3).

The mixture is withdrawn at the discharge valve 15. The container 14, however, can in a given case also serve as reaction container for a further treatment or reaction.

However, it is also possible to apply reduced or excess pressure directly into the discharge line 13 through the known apparatuses and to transport away in known manner the discharging mixture from line 13 while eliminating an intermediate connection from container 14.

The apparatuses 5 and 14 shown in FIGS. 1 and 3, in a given case also line 13, can be heated or cooled in known manner, according to the requirements, see e.g., Ullman, Enzyklopadie der technischen Chemie, Vol. 1, 3rd edition, 1951 pages 743–744 and 769–770.

Likewise there can be used for this purpose the known construction materials, loc. cit.

The volume of the tubular container 5 is determined by the properties of the liquid used whereby the path of the sprayed particles 6 up to the impingement on the liquid layer 4 should be held as short as possible.

Through this it is possible to carry out relatively large throughputs in a very small tubular container, e.g. the volume in Example 1 is about 1.2 liters.

At reduced pressure a portion of the solvent evaporates through which a cooling of the solution or suspension forming takes place. The mixing temperature in this way lets itself be held readily to a low level which is very essential for a continuous procedure.

As water containing organic solvents there are intended solvents having a water content of at least 0.1 weight % water.

However, there are also included in this concept customary industrial solvents which can contain up to 50 weight % water.

These types of solvents are for example, the straight or branched chain alkanes having 5 to 17 carbon atoms, e.g. pentane, hexane, heptane, octane, decane, dodecane, hexadecane, heptadecane, 2-methylheptane, 2,2,4-trimethylpentane, cycloalkanes such as cyclopentane, cyclohexane as well as decalin, aromatic hydrocarbons such as benzene, toluene, xylene, ethyl benzene, halogenated hydrocarbons such a methylene chloride, chloroform, carbon tetrachloride, monochloroethylene, dichloroethylene, trichloroethylene, tetrachloroethylene, trichloroethane, chlorofluoroalkanes such as trichlorotrifluoroethane, halogenated aromatic hydrocarbons such as chlorobenzenes, e.g., chlorobenzene, and o-dichlorobenzene, chlorofluorobenzenes, o-chlorofluorobenzene, p-chlorofluorobenzene and m-chlorobenzotrifluoride, as well as ketones such as acetone, methyl ethyl ketone, diethyl ketone, methyl isobutyl ketone or cyclohexanone, or esters such as alkyl alkanoates, e.g. ethyl acetate, methyl acetate, butyl acetate, methyl butyrate, methyl propionate or ethers such as diethyl ether, diisopropyl ether, dibutyl ether, methyl butyl ether, dioxane or alcohols, e.g. alkanols such as isopropyl alcohol, methyl alcohol, ethyl alcohol, n-propyl alcohol, and butyl alcohol.

If necessary there can also be produced suspensions or solutions of cyanuric chloride in mixtures of these materials.

Preferred solvents are acetone, or industrial acetone, methyl ethyl ketone, methyl isobutyl ketone, dioxane, benzene, toluene or the mixture acetone-toluene.

The solvents mentioned are added at room temperature or lower temperature up to shortly before the solidification point.

The mixing temperature arising according to the process of the invention generally are in the range of 10° to 15° C. although this can be varied.

The mixing temperature naturally depends on both the mixing ratio "solvent-cyanuric chloride melt" which generally are in the range of 6:1 to 1:1, as well as on the amounts of water which are present in the organic solvent and the, if necessary, applied reduced pressure.

Increasing mixing temperatures and increasing water content naturally favor the hydrolysis, thereby the increasing water content appears to be the parameter having the strongest influence.

A suitable apparatus for the recovery of the mentioned cyanuric chloride suspensions or solutions is described and claimed in Hentschel application No. 94803 filed Nov. 15, 1979 and entitled "Apparatus For Bringing Liquids In Contact", which is operated in the following manner.

As shown in FIG. 1 the liquid cyanuric chloride in supply line 1 is led through a coaxial heater 2 via a unary or binary nozzle 3 into the mixing chamber 5, i.e., the tubular container 5.

Figure 2:
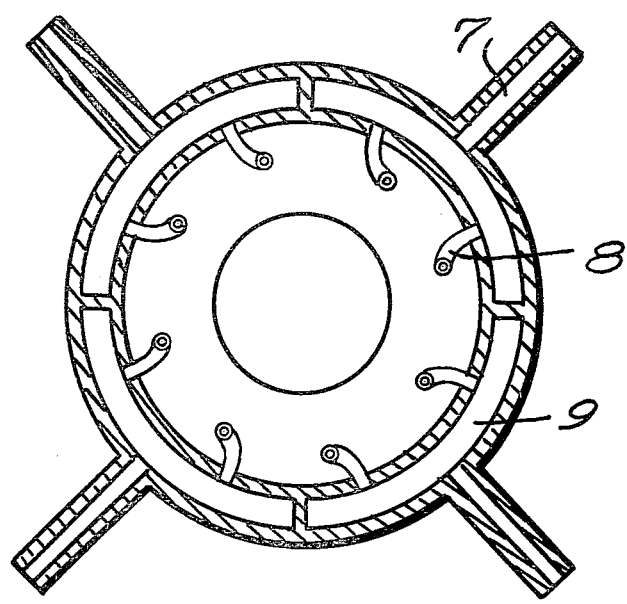
FIG. 2 is a cross-sectional view along the line 2—2 of FIG. 1.

The solvent being brought into contact with the sprayed material goes through separate supply lines 7 into a distribution ring having separate chamber segments 9, see also FIG. 2. The solvent is injected tangentially from these chamber segments via the slightly upwardly directed spray systems into the mixing chamber 5.

When using only one supply and only one spray organ, e.g. opening into the mixing chamber 5, the supply 7 passes directly into the spray opening 8 and the segmented chamber 9 is eliminated.

Besides the component in the circumferential direction the solvent jet has a velocity component in the axial direction. Therethrough the liquid reaches the wall of the mixing chamber 5. There it builds a liquid layer 4.

If different solvents are supplied through the supply lines 7, 8 and 9 into the mixing chamber 5, there occurs here an intensive thorough mixing of the supplied liquids, whose intensity can be increased still more by introducing a gas or vapors of the solvent via the spray system 8.

The cyanuric chloride leaving the nozzle 3 is sprayed into the liquid layer 4. The spray angle for the cyanuric chloride sprayed out of nozzle 3 can be between 15° and 150° C., preferably between 15° and 120° C.

The shape of the spray varies from hollow or solid cone up to an unarranged mist, according to the type of nozzle.

With the entering of the spray particles 6 solidify and/or the sprayed cyanuric chloride dissolves in the liquid layer. The energy brought in is given up to the liquid layer, independent of the pressure in the tubular container.

By establishing a specific pressure, such as a reduced pressure, in the tubular shaped container 5 the heat energy of the sprayed cyanuric chloride in contact with the liquid layer can be carried away.

The suspension or solution of cyanuric chloride produced in the particular solvent leaves the mixing chamber through the discharge outlet 12.

To improve the formation of the solvent layer the spray systems 8 tangential to the mixing chamber are directly slightly upwardly. The exact angle of bending is so adjusted according to the solvent that the liquid layer reaches up to the nozzle, but does not touch it.

Through the breast shaped constriction and the thicker liquid layer produced at this wall position thereby there results, despite the outlet opening, that the remaining chamber walls always are covered with a uniform, i.e. uninterrupted layer of solvent. Through this there is guaranteed a high mixing velocity.

The spray cone of the liquid cyanuric chloride is designated by the number 6.

The number of inlet lines 7 depends on the particular case.

Thus in feeding in only a single material one supply line is sufficient, however, for better distribution of this material there has also proven as desirable to use several supply lines, see for example FIG. 2; even using several components which also can be simultaneously introduced as a mixture the distribution ring described for example in FIG. 2 is suitable.

Liquid cyanuric chloride can be obtained according to known process, e.g. according to Geiger, German Pat. No. 2,322,636 and related Geiger U.S. Pat. NO. 3,925,377. The entire disclosure of the Geiger U.S. patent is hereby incorporated by reference and relied upon.

Preferably according to the process of the invention there is employed a liquid cyanuric chloride whose temperature is 170° C. and which is free from chlorine and cyanogen chloride. For freeing from chlorine and cyanogen chloride known processes are suitable, as e.g. dephlegmatization.

The suspensions and solutions of cyanuric chloride produced according to the invention in leaving the apparatus have a very slight degree of hydrolysis since the residence times and recovery temperatures can be held very low.

These kinds of suspensions or solutions at the temperatures with which they leave the apparatus, depending on the water content of the solution can be stored up to hours.

The resulting suspensions besides are very fine-grained, any formation of clumps is avoided.

In this way, there can be produced at will suspensions or solutions of cyanuric chloride continuously according to the requirements of the moment.

Unless otherwise indicated all parts and percentages are by weight.

The process can comprise, consist essentially of or consist of the steps set forth and the materials can comprise, consist essentially of or consist of those set forth.

The invention will be further explained through the following examples.

DESCRIPTION OF THE PREFERRED EMBODIMENTS

EXAMPLE 1

Liquid cyanuric chloride at about 170° C. is led via the heated supply line 1 into the unary nozzle 3. This nozzle 3 has a bore of 2.6 mm and spray angle of about 78° C. The supply pressure of the liquid cyanuric chloride was 4.5 bar. There were sprayed 340 kg/h of liquid cyanuric chloride through the nozzle 3 into the mixing chamber 5. This mixing chamber 5 has a diameter of 100 mm, the pressure of the mixing chamber was 0.13 bar.

1100 liters/h of acetone containing 2 weight % of water via four different supply lines 7 arrived at the chamber segments 9 and after leaving from eight small tubes 8 formed a liquid layer 4 in the mixing chamber 5.

The suspension of cyanuric chloride and acetone left the mixing chamber 5 through the pipe 12. The concentration of cyanuric chloride in the suspension was 28.4 weight %, the temperature of the discharging suspension was 14° C.

After standing for one hour the degree of hydrolysis of the cyanuric chloride was below 0.3%.

The particle spectrum determined photographically did not show any particle above 100 microns.

EXAMPLE 2

The experimental conditions were changed compared to Example 1 in that the bore of the cyanuric chloride nozzle was 1.0 mm, the spray angle about 45°; the cyanuic chloride supply pressure 1.9 bar; the amount of cyanuric chloride 33.4 kg/h; the diameter of the mixing chamber 50 mm and the acetone mixture was 82 l/h. The acetone supply took place only over one small tube 8 and the supply line 7 while there were introduced 300 l/h of nitrogen via an additional small tube 8 and an additional supply line 7. The water content of the acetone employed was 0.5 weight percent.

The resulting cyanuric chloride concentration was 34 weight %. The temperature of the discharging suspension was about 13° C.

After the mixture stood for one hour at the mixing temperature the degree of hydrolysis of the cyanuric chloride was below 0.3%.

EXAMPLE 3

The experimental conditions were the same as in Example 2 with the following changes.

The water content of the acetone was 20 weight % and the resulting cyanuric chloride concentration was 34 weight %. The cyanuric chloride suspension was cooled to minus 20° C. within 5 minutes and after standing for one hour had a degree of hydrolysis of the cyanuric chloride below 0.5%.

The particle spectrum determined photographically showed no particles above 100 microns.

EXAMPLE 4

The experimental conditions were the same as in Example 1 with the following changes:

The bore of the cyanuric chloride nozzle was 1.1 mm, the spray supply pressure 6.0 bar and the amount of cyanuric chloride 40.5 kg/h. 608 kg/h of acetone were supplied to the mixing chamber 5 via two supply lines 7 with four small tubes 8 and there were supplied to the mixing chamber via two supply lines 7 and 4 small tubes 8 259 kg/h of toluene.

The resulting cyanuric chloride concentration was 4.5%.

After the solution of cyanuric chloride stood for one hour the degree of hydrolysis of the cyanuric chloride was below 0.3%.

EXAMPLE 5

The experimental conditions were the same as in Example 1 with the following changes:

The bore of the cyanuric chloride nozzle was 1.85 mm, the supply pressure of the spray 6.0 bar and the amount of cyanuric chloride 118 kg/h. In place of acetone there were employed 980 kg/h of methyl ethyl ketone.

The resulting cyanuric chloride concentration in this test material was 10.7%.

What is claimed is:

1. A process for the production of a suspension or solution of cyanuric chloride in a water containing organic solvent comprising spraying cyanuric chloride downwardly and outwardly at a temperature in its molten range from the upper portion of a vertical tubular zone closed at the top thereof to contact and mix with water containing organic solvent which forms a liquid layer defining, said tubular zone, constricting said layer in breast-shaped manner downwardly below the place of entry of the cyanuric chloride into the tubular zone to form a narrower discharge opening, discharging water containing organic solvent as a spray tangentially to said layer and directed slightly upwardly in the direction of the closed top above said constriction and point of introduction of the cyanuric chloride and thereby forming said liquid layer along the entire tubular zone to the point of introduction of the cyanuric chloride, whereby the thickness of said layer where it is formed in the breast-shaped constriction is greater than it is in the remainder of the tubular zone.

2. The process of claim 1 wherein the liquid cyanuric chloride employed is free from chlorine or cyanogen chloride.

3. The process of claim 2 wherein the water content of the solvent is 0.1 to 50 weight %.

4. The process of claim 1 wherein the content of the solvent is 0.1 to 50 weight %.

5. The process of claim 1 wherein the water containing solvent is an aliphatic or cycloaliphatic ketone having 3 to 6 carbon atoms.

6. The process of claim 5 wherein the ketone is acetone, methyl ethyl ketone or methyl isobutyl ketone.

7. The process of claim 6 wherein the ketone is acetone or methyl ethyl ketone.

8. The process of claim 1 including reducing the pressure to between below atmospheric pressure and 0.01 bar and thereby lowering the mixing temperature.

9. A process according to claim 1 comprising discharging the solution or suspension formed to another container adapted for use at subatmospheric or superatmospheric pressure.

* * * * *